(12) United States Patent
Reynolds et al.

(10) Patent No.: US 7,154,592 B2
(45) Date of Patent: Dec. 26, 2006

(54) MULTIWAVELENGTH READHEAD FOR USE IN THE DETERMINATION OF ANALYTES IN BODY FLUIDS

(75) Inventors: Jeffery S. Reynolds, Granger, IN (US); Andrew J. Dosmann, Granger, IN (US)

(73) Assignee: Bayer Healthcare LLC.DE (US)

( * ) Notice: Subject to any disclaimer, the term of this patent is extended or adjusted under 35 U.S.C. 154(b) by 254 days.

(21) Appl. No.: 10/770,059

(22) Filed: Feb. 2, 2004

(65) Prior Publication Data

US 2004/0157341 A1  Aug. 12, 2004

Related U.S. Application Data

(60) Provisional application No. 60/446,279, filed on Feb. 11, 2003.

(51) Int. Cl.
*G01N 33/48*  (2006.01)

(52) U.S. Cl. .......................................... 356/39; 356/40

(58) Field of Classification Search ...................... None
See application file for complete search history.

(56) References Cited

U.S. PATENT DOCUMENTS

| | | | | |
|---|---|---|---|---|
| 5,303,037 A | * | 4/1994 | Taranowski | ................. 356/406 |
| 5,305,093 A | | 4/1994 | Dosmann | ..................... 356/435 |
| 5,349,504 A | | 9/1994 | Simms et al. | |
| 5,945,676 A | * | 8/1999 | Khalil et al. | ........... 250/339.12 |
| 6,373,568 B1 | * | 4/2002 | Miller et al. | ................. 356/326 |
| 6,630,947 B1 | * | 10/2003 | Lieberman et al. | ........... 348/85 |
| 6,741,875 B1 | * | 5/2004 | Pawluczyk et al. | ......... 600/310 |
| 6,833,540 B1 | * | 12/2004 | MacKenzie et al. | ..... 250/214.1 |
| 6,879,399 B1 | * | 4/2005 | Yamauchi | ..................... 356/344 |
| 6,954,260 B1 | * | 10/2005 | Arnold et al. | ................. 356/71 |
| 2001/0043780 A1 | | 11/2001 | Gancarcik et al. | |
| 2004/0147034 A1 | * | 7/2004 | Gore et al. | ................... 436/95 |

FOREIGN PATENT DOCUMENTS

| | | |
|---|---|---|
| EP | 0 299 314 A2 | 1/1989 |
| EP | 0 866 329 A2 | 9/1998 |
| WO | WO 97/41421 | 11/1997 |

* cited by examiner

*Primary Examiner*—Michael P. Stafira
(74) *Attorney, Agent, or Firm*—Jenkens & Gilchrist

(57) ABSTRACT

A readhead for use in the determination of the concentration of an analyte in a sample comprises a read area for receiving the sample, a light source including a plurality light emitting elements for outputting light at a plurality of wavelengths, a light guide having an input end and an output end, a lens for receiving light from the output end of the light guide and for illuminating the sample with a substantially collimated beam of light, and a detector for detecting light from the sample in response to illuminating the sample. The input end of the light guide being optically coupled to the light source for receiving light output by the plurality of light emitting elements. The input end of the light guide has a center that is offset from the center of at least one of the plurality of light elements. The light guide guides a substantial portion of the light received from the light source to the output end of the light guide.

67 Claims, 9 Drawing Sheets

MULTIWAVELENGTH READHEAD FOR USE IN THE DETERMINATION OF ANALYTES IN BODY FLUIDS

RELATED APPLICATION

This application claims the benefit of the U.S. Provisional Application 60/446,279, filed on Feb. 11, 2003 and entitled "Multiwavelength Readhead For Use In The Determination Of Analytes In Body Fluids", which is hereby incorporated by reference in its entirety.

FIELD OF THE INVENTION

The present invention relates generally to testing systems for determining the concentration of an analyte in a biological sample, and more particularly, to an optical readhead for use in determining the concentration of an analyte in a biological sample.

BACKGROUND OF THE INVENTION

It is often necessary to quickly obtain a sample of blood and perform an analysis of the blood sample. One example of a need for obtaining a sample of blood is in connection with a blood glucose monitoring system, which a user must frequently use to monitor the user's blood glucose level.

Those who have irregular blood glucose concentration levels are medically required to regularly self-monitor their blood glucose concentration levels. An irregular blood glucose level can be brought on by a variety of reasons including illness such as diabetes. The purpose of monitoring the blood glucose concentration level is to determine the blood glucose concentration level and then to take corrective action, based upon whether the level is too high or too low, to bring the level back within a normal range. The failure to take corrective action can have serious implications. When blood glucose levels drop too low—a condition known as hypoglycemia—a person can become nervous, shaky and confused. That person's judgment may become impaired and that person may eventually pass out. A person can also become very ill if their blood glucose level becomes too high—a condition known as hyperglycemia. Both conditions, hypoglycemia and hyperglycemia, are potentially life-threatening emergencies.

One method of monitoring a person's blood glucose level is with a portable, hand-held blood glucose testing device. The portable nature of these devices enables users to conveniently test their blood glucose levels wherever the users may be. Typically, these devices can employ either electro-chemical testing or colorimetric testing. In an electrochemical assay, a regent is designed to react with glucose in the blood to create an oxidation current at electrodes disposed within the reaction area. The current is directly proportional to the concentration of glucose in the user's blood. In a calorimetric assay, a reagent is designed to produce a colorimetric reaction indicative of a user's blood glucose concentration level. An optical instrument incorporated into the testing device then reads the colorimetric reaction.

Drawbacks associated with optical instruments for reading colorimetric reactions include size, low signal throughput and accuracy errors which are due, in part, to mechanical alignment (or mis-alignment) sensitivity of the optical components. These problems are further compounded when the optical instruments require readings at more than one wavelength. Providing multiple wavelengths compounds these problems because prior art devices produce light of each wavelength with a different light elements such as a light emitting diodes. It is difficult and expensive for multiple light emitting diodes to be aligned to provide identical illumination of the sample area. Misalignment and source geometry variations result in the light from each of the light emitting diodes having a different irradiances and different irradiance distributions across the sample. Thus, what is needed is a device than can illuminate a sample with a plurality of wavelengths of light, wherein each of the beams of light of different wavelengths have substantially uniform irradiances and irradiance distributions across the sample.

SUMMARY OF THE INVENTION

A readhead for use in the determination of the concentration of an analyte in a sample comprises a read area for receiving the sample, a light source including a plurality light emitting elements for outputting light at a plurality of wavelengths a light guide having an input end and an output end, a lens for receiving light from the output end of the light guide and for illuminating the sample with a substantially collimated beam of light, and a detector for detecting light from the sample in response to illuminating the sample. The input end of the light guide being optically coupled to the light source for receiving light output by the plurality of light emitting elements. The input end of the light guide has a center that is offset from the center of at least one of the plurality of light elements. The light guide guides a substantial portion of the light received from the light source to the output end of the light guide.

The above summary of the present invention is not intended to represent each embodiment, or every aspect, of the present invention. Additional features and benefits of the present invention will become apparent from the detailed description, figures, and claims set forth below.

DETAILED DESCRIPTION OF THE ILLUSTRATED EMBODIMENTS

Figure 1:
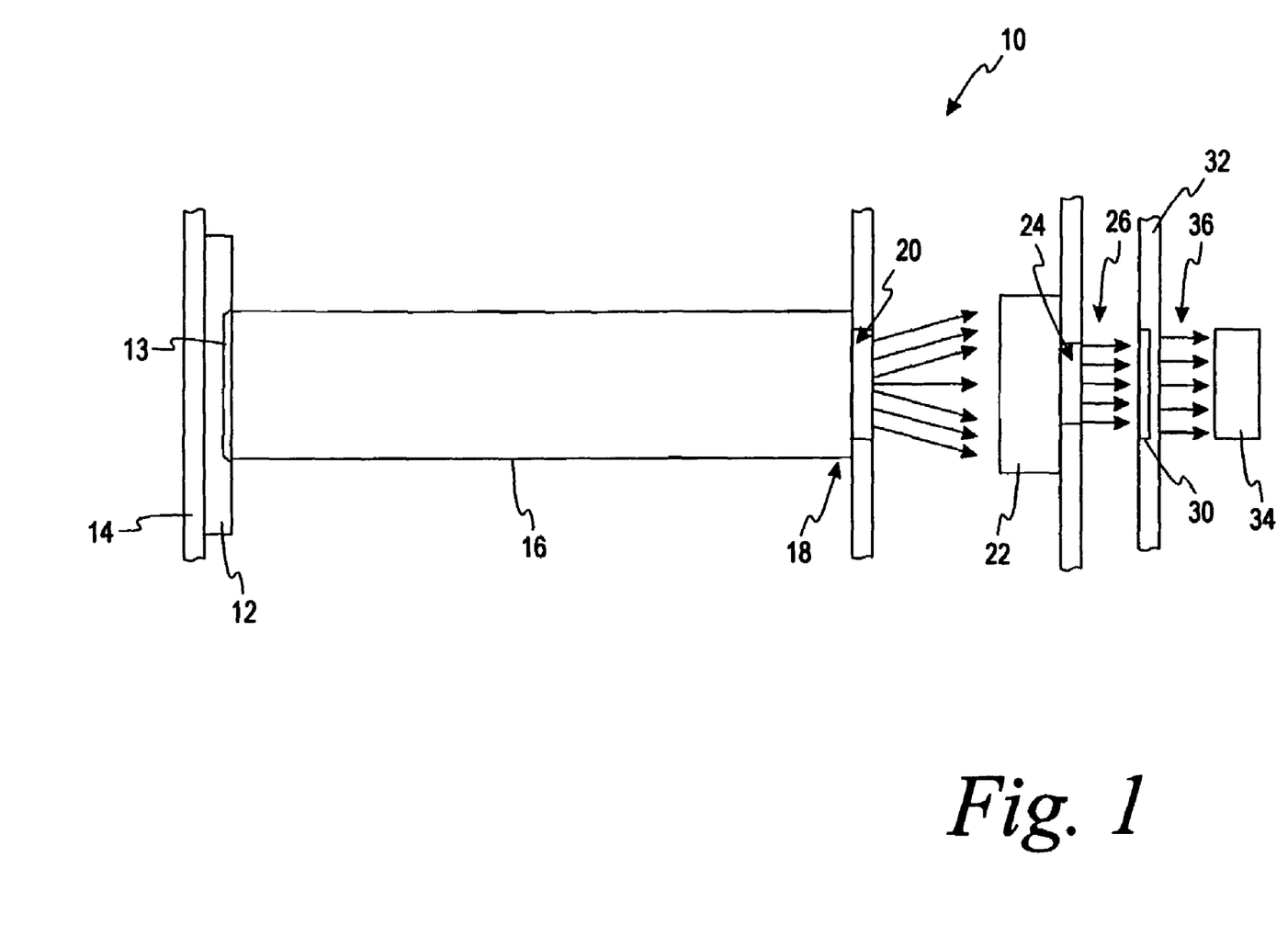
FIG. 1 is a functional block diagram of a multiwavelength transmission readhead according to one embodiment of the present invention.

Turning now to the drawings and initially to FIG. 1, there is shown a multiwavelength readhead 10 according to one embodiment of the present invention. In one application the readhead 10 is included in a portable, handheld glucose testing device for measuring the glucose concentration in the body fluid of a patient (who is also the user in self-testing applications. Specifically, the readhead 10 is used for measuring a colorimetric reaction when a reagent reacts with an analyte. The readhead 10 of the present invention is used in the measuring of the degree of color change of the reagent resulting from the reaction. The degree of color change of the regent is indicative of the concentration of the analyte (e.g, glucose, fructosamine, hemoglobin Alc, cholesterol, etc.) in the body fluid. Colorimetric testing is described in detail in U.S. Pat. No. 5,723,284 entitled "Control Solution And Method For Testing The Performance Of An Electrochemical Device For Determining The Concentration Of An Analyte In Blood," which is incorporated herein by reference in its entirety. Colorimetric testing is also described in detail in U.S. Pat. No. 6,181,417 B1 (entitled "Photometric Readhead with Light Shaping Plate"), U.S. Pat. No. 5,518,689 (entitled "Diffuse Light Reflectance Readhead"), and U.S. Pat. No. 5,611,999 (entitled "Diffuse Light Reflectance Readhead"), each of which is incorporated herein by reference in its entirety.

The readhead 10 includes a light source that includes a surface mount light emitting diode 12 ("SMD LED") according to one embodiment of the present invention. The SMD LED 12 is mounted on a printed circuit board 14 ("PCB"), which can include the electronics that run the operation of the device that the readhead 10 of the present invention is contained within. The SMD LED 12 is a multiwavelength SMD LED that outputs light at a plurality of wavelengths such as, for example, red, green, and blue. According to one embodiment, the surface mount device includes a red LED for outputting red light having a wavelength of ranging between about 600 nanometers ("nm") and about 670 nm, a green LED for outputting green light having a wavelength ranging between about 520 nm and about 580 nm, and a blue LED for outputting a blue light having a wavelength ranging between about 360 nm and about 450 nm. According to another embodiment, the red light has a wavelength of about 625 nm, the green light has a wavelength of about 565 nm and the blue light has wavelength of about 430 nm. According to yet another alternative embodiment of the present invention, the surface mount device includes an infrared LED for outputting infrared light having a wavelength ranging between about 800 nm and about 1000 nm. A SMD LED suitable for use with the readhead 10 is available from Kingbright Corporation of City of Industry, Calif., model number AAA3528EMBSGC. According to an alternative embodiment, the light source can include other types of light sources besides LEDs. For example, multiple packaged LEDs, multiple chip-on-board LED's, or laser diodes can be used as sources to output light at a plurality of wavelengths.

Multiple wavelengths of light output by the SMD LED 12 illuminate a sample as described in further detail below. Instrument performance is improved by illuminating a sample with light of multiple wavelengths because the intervening wavelengths can be used to correct errors in the particular wavelength used to evaluate the sample. For example, when the sample is blood, particular wavelengths of light are more greatly absorbed in the about 400 nm to about 600 nm range (and in other ranges) by naturally occurring chromophores like hemoglobin. The accuracy of a calorimetric measurement is limited by the absorption caused by unknown levels of the interfering absorbers. For example, the hematocrit content of blood is known to vary over a wide range from sample to sample and subject to subject. In cases where pure interstitial fluid samples are obtained, the hematocrit content approaches zero. The strong absorption of the hemoglobin in the hematocrit causes a widely varying "background" absorption that can not be distinguished from absorption changes in the colorimetric reagents of interest. However, properly chosen auxiliary wavelengths can be used to compensate for measurements at the wavelength of interest by, for example, a ratio of the absorption at the two wavelengths for example. In addition, multiple auxiliary wavelengths can be used to compensate for other phenomena that interfere with an absorption measurement like mechanical misalignment, variations in scattering from the sample, and variations in scattering from scattering membranes in diffuse reflection measurements.

The SMD LED 12 inputs light to a light guide 16 for directing the light to a sample. According to one embodiment of the present invention, molded with an optically clear material such as, for example, acrylic. In other embodiments, the light guide 16 is molded with other optically clear materials such as, for example, polycarbonate, or polyester. Light from the SMD LED 12 reflects out of the SMD LED 12 off a white conical reflector 13 in the SMD LED 12. The light is guided down the light guide 16 by total internal reflection. The light guide 16 provides the advantage of being able to deliver at its output end 18 a significant amount of the light that is input to the light guide 16 by the SMD LED 12. According to one embodiment of the present invention, the light guide 16 has a square cross-section with dimensions of about 2.3 mm by about 2.3 mm and a length of about 5 cm. A conical reflector 13 of the SMD LED 12 has a diameter of about 2.4 mm according to one embodiment of the present invention. The SMD LED 12 and the light guide 16 are closely coupled resulting in about ninety-two percent of the light output by the SMD LED 12 being captured by the light guide 16.

Figure 3A:
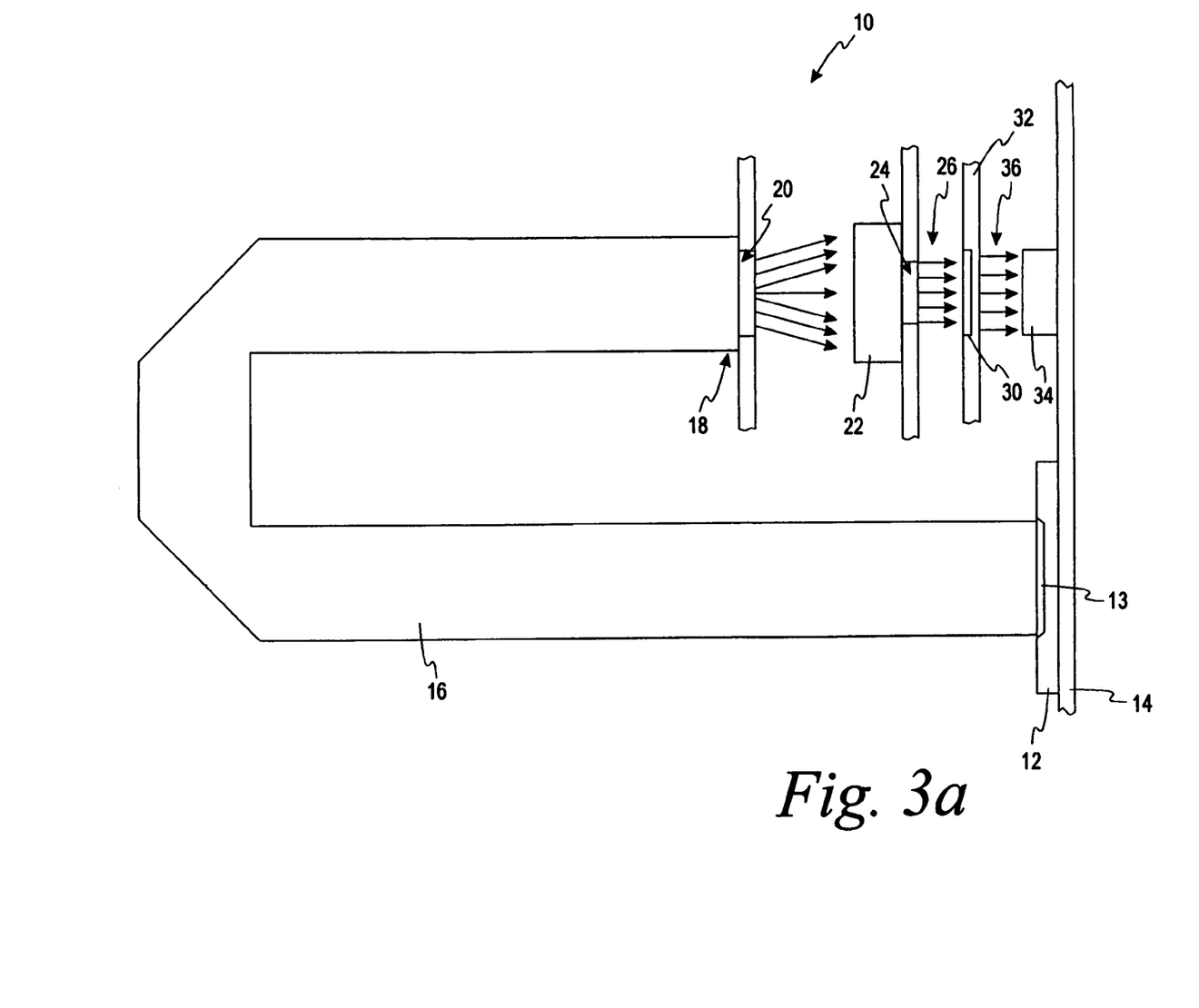
FIG. 3a is another alternative embodiment of the readhead shown in FIG. 1.
Figure 3B:
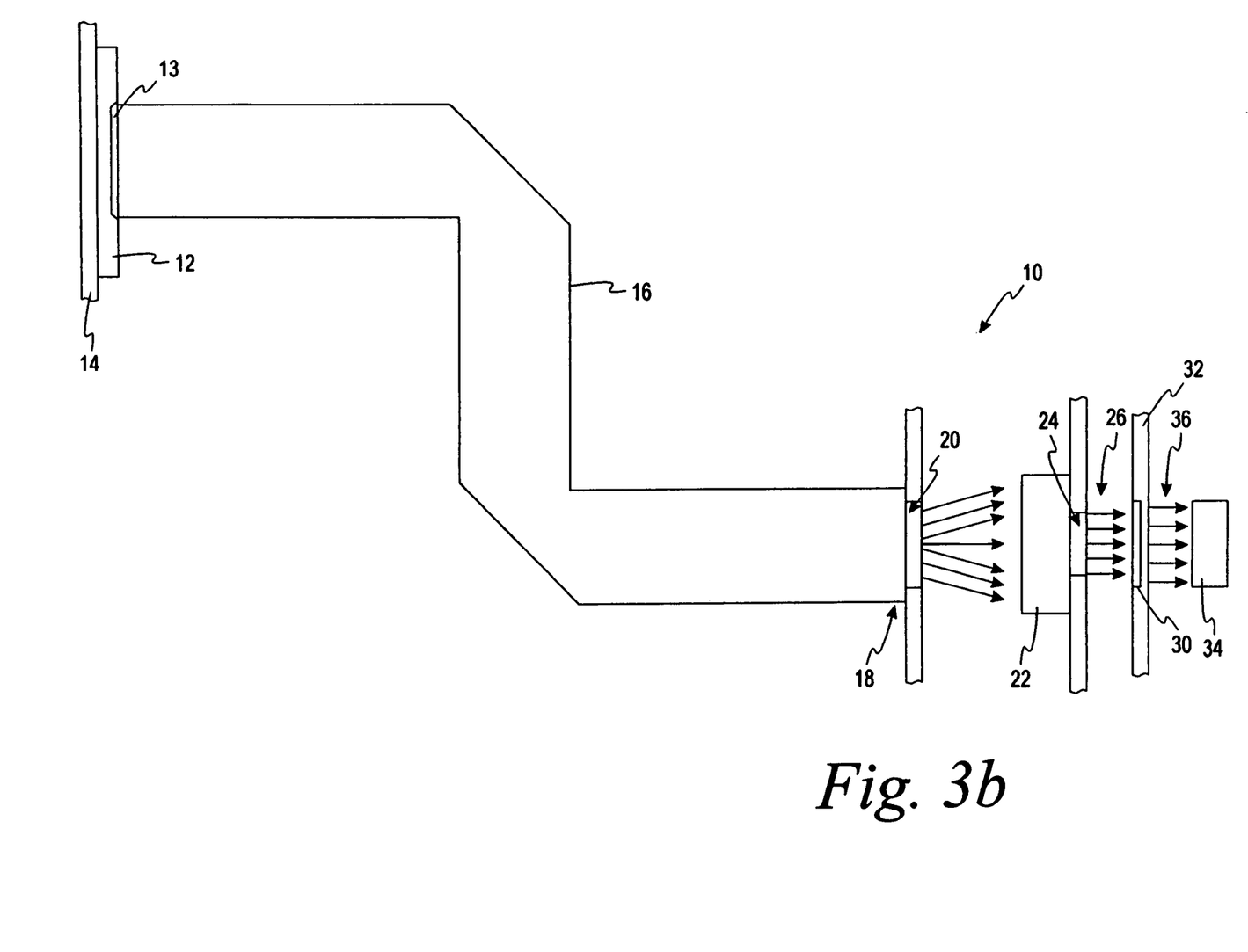
FIG. 3b is another alternative embodiment of the readhead shown in FIG. 1.

The light guide 16 depicted in FIGS. 3a and 3b is bent to illustrate that the light guide 16 can be molded in a fashion to follow a path having one or more about 90 degree bends without a significant degradation in the intensity of the delivered light nor a significant disruption in the illumination distribution of the delivered light. The nature of the light guide 16 allows for the light source 12 and the sample being illuminated to be disposed along a non-linear illumination path. In alternative embodiments, the light guide 16 is disposed along a non-linear path having angles other than right angles The light guide 16 delivers light from the SMD LED 12 to collimation optics at the output end 18 of the acrylic light guide 16. The collimation optics include a body having a collimation aperture 20 and a collimation lens 22, which outputs a substantially collimated beam of light. The collimated beam of light is directed through a sample aperture 24 disposed in another body for reducing the diameter of the collimated beam of light—this narrowed, substantially collimated beam of light is labeled with reference number 26. A collimation lens 22 suitable for use with one embodiment of the readhead 10 shown in FIG. 1 is available from Edmund Industrial Optics of Barrington, N.J., stock number NT45-117, which is a glass plano convex lens having a three millimeter focal length.

The collimated beam of light 26 exiting the sample aperture 24 is directed onto a biological sample (e.g., blood, intercellular material, extracellular fluid, interstitial fluid, a combination thereof, etc.) that is disposed in a read area 30 of a sample format 32. The biological sample includes an analyte that reacts with a reagent also disposed in the read area. (A reagent is disposed within the read area 30 prior to each use.) According to one embodiment of the present invention, the sample format 32 collects the sample from a patient. For example, the fingertip of a patient is lanced and a drop of blood is produced on the patient's fingertip. The format 32 is brought into contact with the drop of blood and collects the blood via a capillary channel (not shown), for example, that draws the blood to the read area 30 of the format 32 where an analyte (e.g., glucose) within the blood reacts with the reagent disposed in the read area 30 of the format 32. Alternatively, the biological sample is directly placed in the read area 30 by a separate collection device.

Alternatively still, the biological sample (e.g., blood) containing an analyte (e.g., glucose) is harvested using a test strip having a reagent disposed therein. The blood moves into the test sensor and the analyte reacts with the reagent to produce a colorimetric reaction. The test sensor is then inserted into the read area 30 of the readhead 10 for analysis. In the embodiment of the readhead 10 shown in FIG. 1, wherein light transmitted through the sample is measured, at least the portion of the test sensor wherein the colorimetric reaction takes place is constructed of a substantially optically clear material. In the embodiment of the readhead 100 shown in FIG. 8, wherein light reflected from the sample is measured as is discussed below, the backside of the test sensor wherein the calorimetric reaction takes place should be constructed of a diffusely reflective material while the front slide of the test strip should be constructed of a substantially optical clear material; such a construction allows the light to illuminate the sample and reflect from the sample.

Referring back to FIG. 1, the substantially collimated light 26 directed onto a sample disposed in the read area 30 of the format is transmitted though the sample and through read area 30 and onto a detector 34. The transmitted light is labeled with reference number 36. Because light is transmitted through the format, the format 32 is constructed of an optically clear material so that the format 32 does not significantly alter or degrade the transmitted light 36. The format 32 can be molded with optically clear materials such as acrylic, polycarbonate or polyester, for example.

The light 36 transmitted through the sample is received by the detector 34 that outputs a signal indicative of the received light. A CMOS monolithic detector/amplifier available from Texas Advanced Optoelectronic Solutions, Inc., model number TAOS TSL250R, is suitable for use as the detector 34 according to one embodiment of the present invention. The signal indicative of the received light is output by the detector 34 onto a lead (not shown) that is electronically coupled to the electronics of the device housing the readhead 10.

The signal output by the detector is compared to a reference signal stored in a memory (not shown) of the device housing the readhead 10. The reference signal is obtained by illuminating the read area 30 prior to placing the sample in the read area 30. The reference signal is then compared to the signal obtained from the light transmitted through the sample. The difference in light absorption between the two is used to determine the concentration of the particular analyte in the sample being evaluated.

According to one embodiment of the present invention, the readhead 10 is constructed with the following dimensions: the light guide 16, constructed of acrylic, has an about 2.3 mm by about 2.3 square cross-section and a length about 5 cm; the collimation aperture 24 has a diameter of about 0.76 mm; and the sample aperture 24 has a diameter of about 0.5 mm resulting in a beam of light having a diameter of about 0.75 mm for illuminating the read area 30 which is located about 2 mm away from the sample aperture 24. The dimensions of the readhead 10 can vary according to alternative embodiments of the present invention and the particular dimensions described are provided by way of example. Components can be scaled accordingly to accommodate more LED wavelengths and/or light beam shapes and sizes in various alternative embodiments of the present invention.

Figure 2:
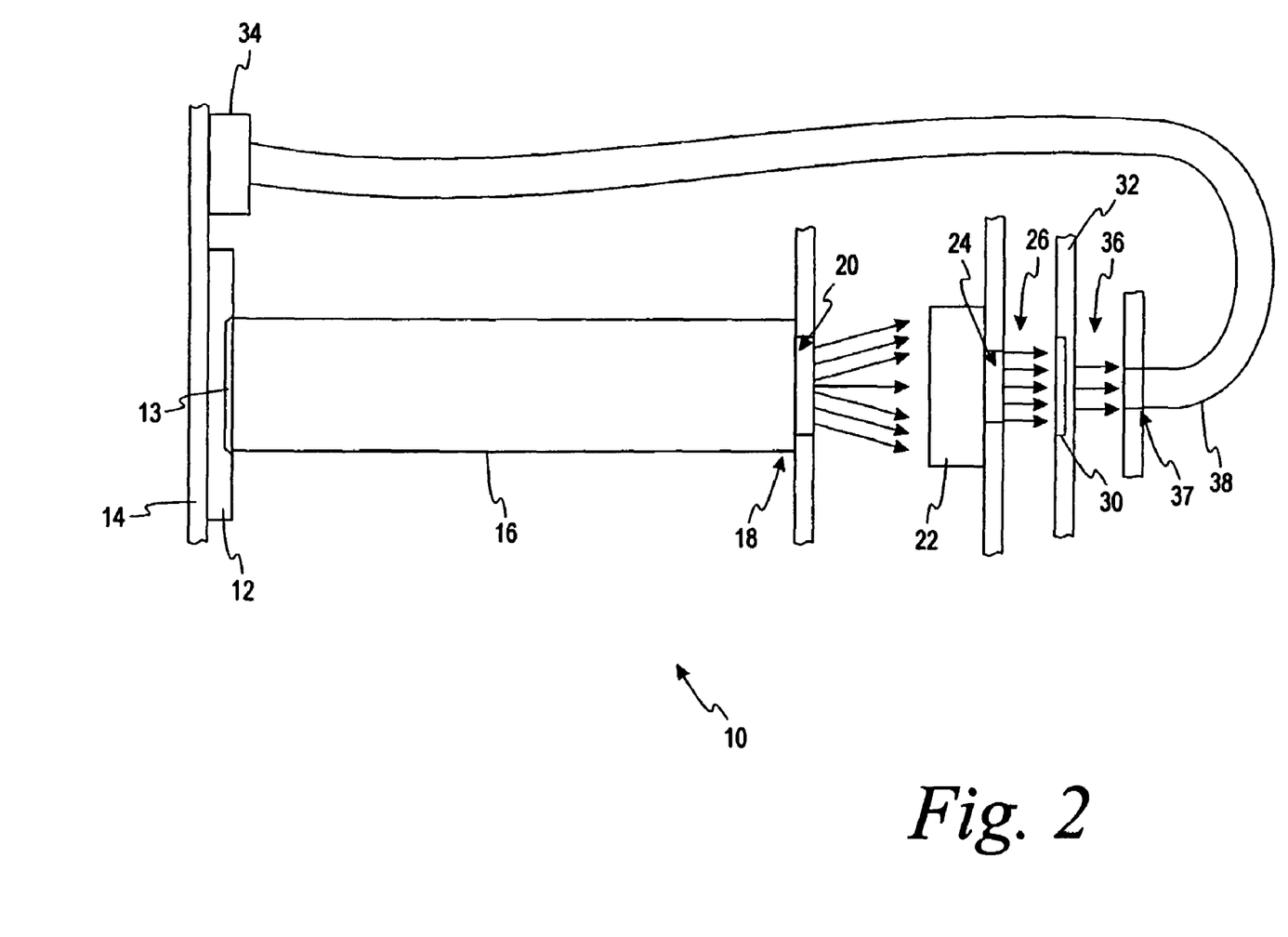
FIG. 2 is an alternative embodiment of the readhead shown in FIG. 1.

Referring now to FIG. 2, according to an alternative embodiment of the readhead 10, the detector 34 is disposed on the PCB 14 along with the other electronics of the device that contains the readhead 10. An aperture 37 receives the transmitted light 36 as it is output form the format 32 and inputs that light to a fiber optic cable 38 which pipes the transmitted light to a detector 34 disposed on the PCB 14. A fiber optic cable 38 suitable for use with the embodiment of the readhead 10 shown in FIG. 2 is available from Edmund Industrial Optics of Barrington, N.J., stock number NT02-535. Such an embodiment provides the advantage having the electronics disposed on the same PCB 14 and in the same location within the device.

Referring now to FIG. 3a, there is shown another alternative embodiment of readhead 10. As in the alternative embodiment discussed in connection with FIG. 2, the embodiment shown in FIG. 3a includes both the SMD LED 12 and the detector 34 disposed on the PCB 14. However, in the embodiment of the readhead 10 shown in FIG. 3a, the light guide 16 is bent or shaped to deliver light from the SMD LED 12 (disposed on the PCB 14) to the detector 34 (also disposed on the PCB 14). An advantage of the embodiment of the readhead 10 illustrated in FIG. 3 is that it is constructed with a reduced number of parts as a lead (not shown) from the detector 34 to the PCB 14 discussed in connection with FIG. 1, for example, or the fiber optic cable 38 discussed in connection with FIG. 2, for example, are eliminated. Having a non-linear light guide of FIG. 3a is useful in applications where spatial constraints do not allow for a linear light guide.

Referring now to FIG. 3b, there is shown another alternative embodiment of the readhead 10. The readhead of FIG. 3b is similar to that of FIG. 1. The light guide 16 in the embodiment of FIG. 3b, however, includes two substantially ninety degree bends along its path between the SMD LED 12 and the output end 18 of the light guide 16.

The readhead 10 provides the advantage of providing an increased throughput of light from the light source to the read area 30. The throughput is increased by closely coupling between the light source (e.g., the SMD LED 12) and the light guide 16. Even illumination at the output end 18 of the light guide 16 improves the light level at the calumniation aperture 20. Good signal level is maintained through the collimation optics by using micro-optics to substantially collimate the light. According to one embodiment, the substantially collimated sample beam 26 is reduced to a diameter of about 0.75 mm on an about 1 mm diameter sample without reducing the signal to an unacceptable level. An estimate of the signal throughput using a LightTools® software model to simulate the readhead 10 predicts a detector current about 384 nA at a wavelength of about 680 nm.

Transmission accuracy problems can be caused by mechanical alignment variation of the optical components. Sample beam diameter, divergence, intensity distribution, and location of the sample can all lead to accuracy errors. These problems are particularly prevalent when transmission readings are required at two or three wavelengths. The readhead 10 of the present invention reduces these types of errors. Specifically, the square light guide 16 reduces beam geometry and intensity variations related to the use of multiple wavelengths of light output by the multiple LEDs of the SMD LED 12. The non-uniform intensity distribution output of the SMD LED 12 is caused by the LED dies of the SMD LED 12, which do not output light on a common axis. Thus, one or more of the LED dies of the SMD LED 12 are offset from the center of the input end of the light guide 16. A SMD LED 12 with multiple dies, however, is desirable because of its low-cost and its ability to output light at multiple wavelengths. The inventors have found, however, that an acrylic light guide 16 having a square cross-section creates an even illumination distribution for each wavelength at the output end 18 of the guide 16 even though the LED dies of the SMD LED 12 are offset from the center of the light guide 16. Put another way, this arrangement results in a substantially identical beam diameter, divergence and alignment regardless of the wavelength of light output by the SMD LED 12.

Figure 4:
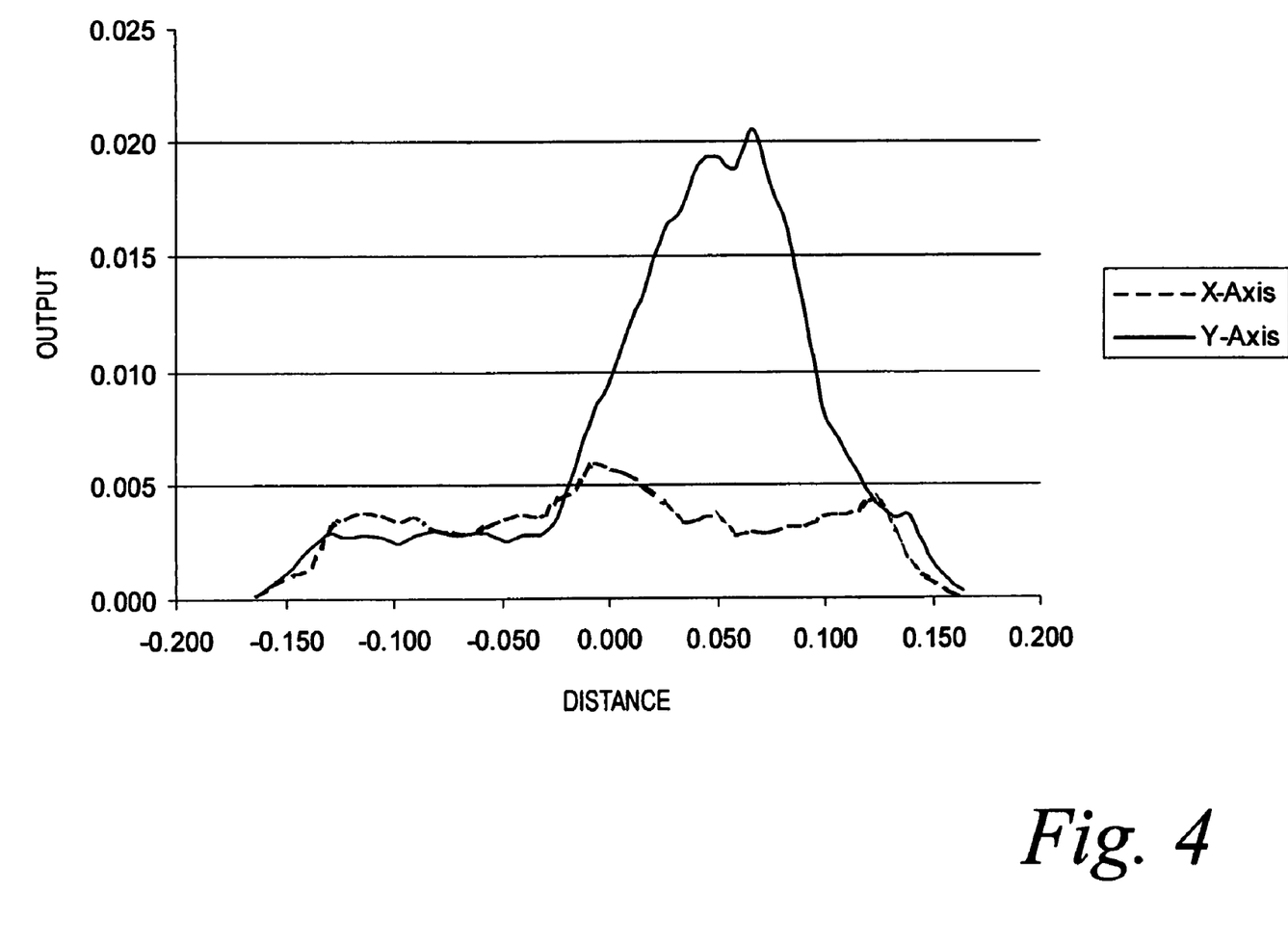
FIGS. 4 and 5 are plots of a modeled illumination intensity distribution of light output by a light source of the readhead shown in FIG. 1 without and with a light guide, respectively.
Figure 5:
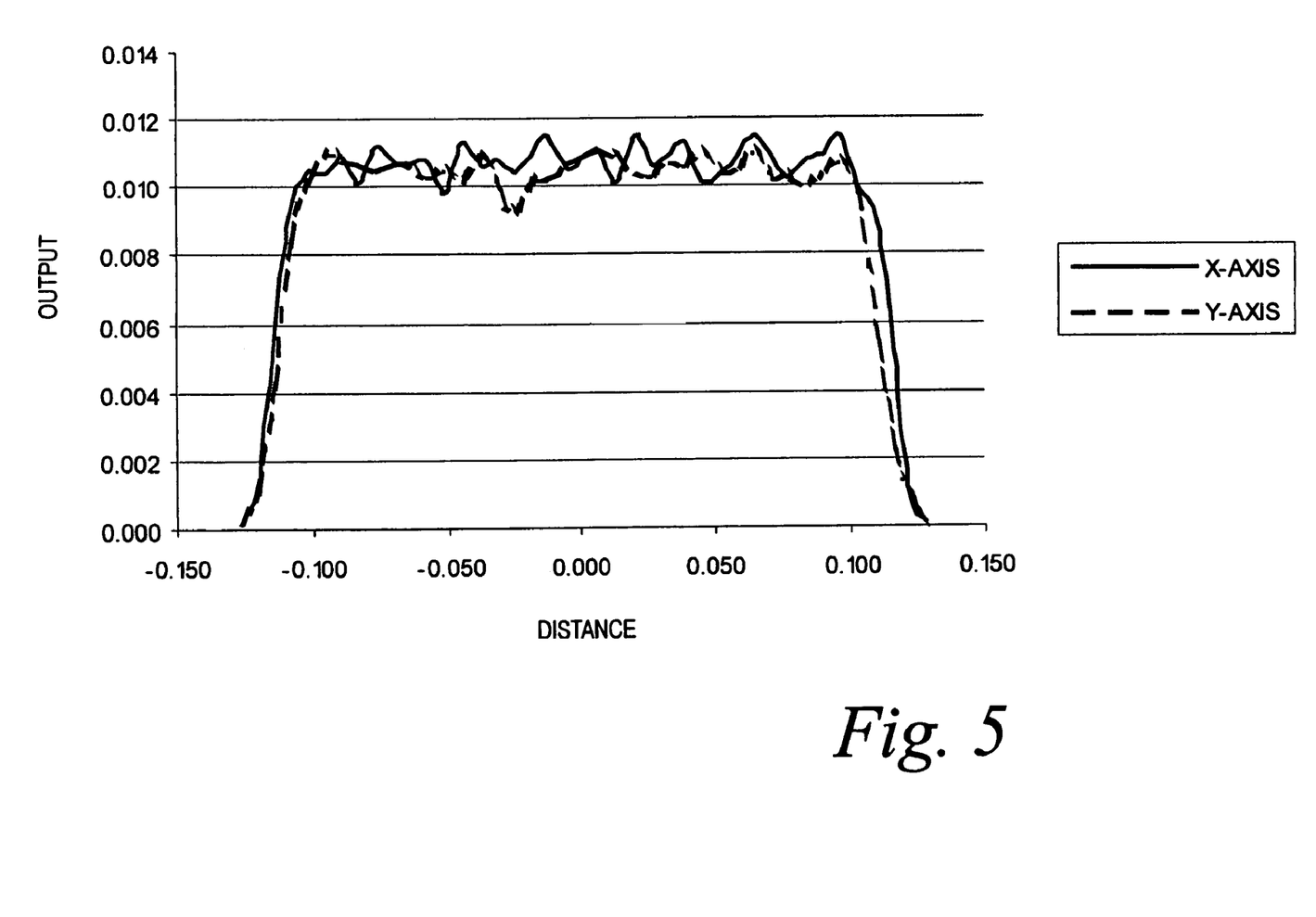

Referring now to FIGS. 4 and 5, the readhead 10 of FIG. 1 was simulated on a computer using a LightTools® software model. The plots illustrate the illumination intensity across the face of the detector 34 along its X-axis and Y-axis without the light guide 16 (FIG. 4) and with the light guide (FIG. 5). The LED dies within the SMD LED 12 are modeled to have an about 0.43 mm offset from the Y-axis of the SMD LED 12 package (to account for the three LED dies within the SMD LED each being offset from center about 0.43 mm within the SMD LED package). FIG. 4 shows that the illumination distribution along the Y-axis of the detector 34 is rather uneven and includes a "hotspot" (i.e., an area of relatively greater intensity) when the light guide 16 is excluded. Along the X-axis of the detector, the intensity distribution is somewhat more uniform; however, the intensity is low without the light guide 16.

As can be seen from FIG. 5, the addition of the light guide 16 results in a significantly improved illumination distribution and intensity across the face of the detector 34, which is due, at least in part, to the successive side wall reflections in the light guide 16. The inventors have found that a light guide of at least 5 cm, which has a cross-section that is about 2.3 mm square, sufficiently increases the number of side wall internal reflections to produce even illumination at the output end 18 of the light guide 16

Figure 6A:
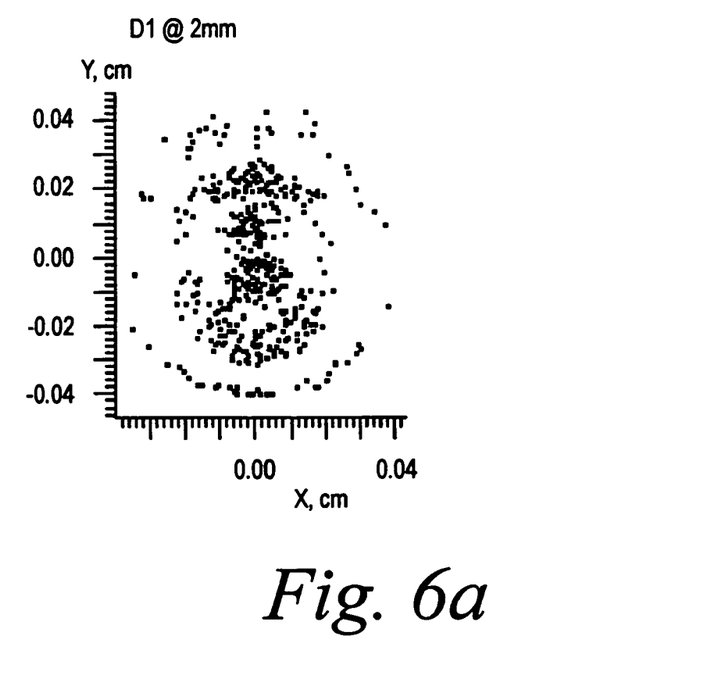
FIGS. 6a, 6b, and 6c are modeled intensity distribution scatter plots of a beam of light output from a sample aperture of the readhead of FIG. 1 detected at distance of two, five and ten millimeters, respectively, from the sample aperture, wherein the light guide of the readhead has a round cross-section.
Figure 6B:
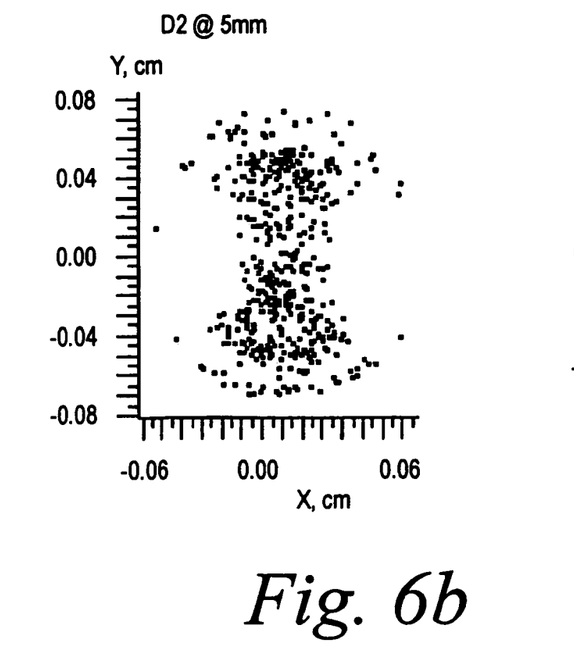
Figure 6C:
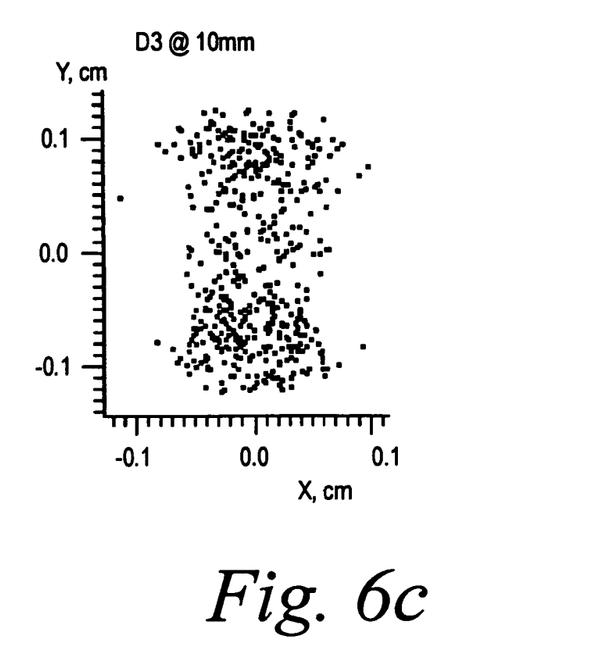
Figure 7A:
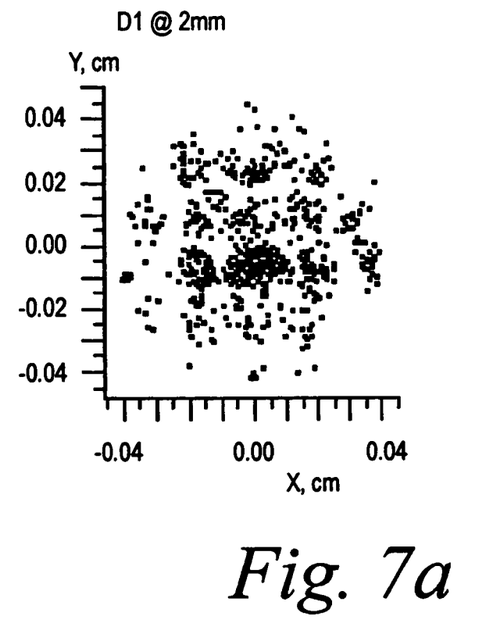
FIGS. 7a, 7b, and 7c are modeled intensity distribution scatter plots of a beam of light output from a sample aperture of the readhead of FIG. 1 detected at distance of two, five and ten millimeters, respectively, from the sample aperture, wherein the light guide of the readhead has a square cross-section.
Figure 7B:
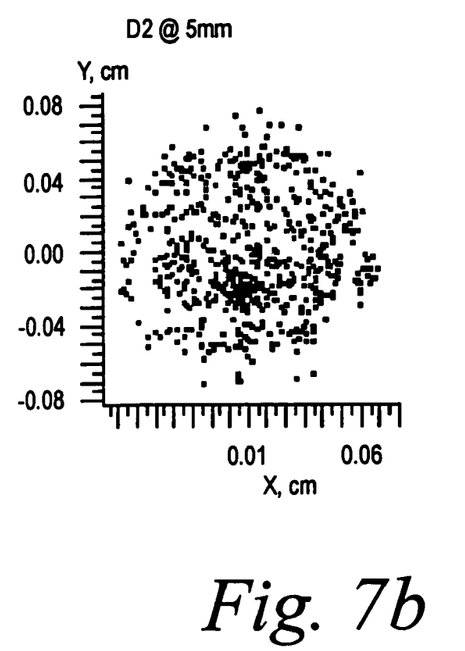
Figure 7C:
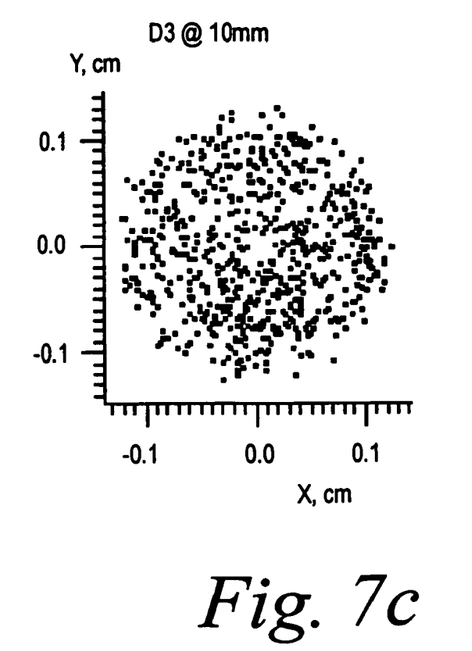

The inventors have also found that a light guide having a square cross-section produces better results than a light guide having a round cross-section. Referring now to FIGS. 6 and 7, intensity distribution plots are shown for the readhead 19 (FIG. 1). However, the readhead 10 used in connection with FIG. 6 implements a light guide 16 having a round cross-section (about 2.3 mm diameter), while the readhead 10 used in connection with FIG. 7 utilized a light guide 16 having a square cross-section (about 2.3 mm by about 2.3 mm). FIGS. 6 and 7 each include three intensity distribution plots corresponding to three different detectors disposed at two, five and ten millimeters for the sample beam aperture 24. The round light guide (FIG. 6) produces non-uniform intensity distributions at each of the three detectors and the distributions are different at each of the detectors. The square light guide (FIG. 7) produces substantially even distributions at each of the three detectors. The irradiance of the round guide is about 4.9 $\mu W/cm^2$ and is about 6.8 $\mu W/cm^2$ for the square guide. Thus, the square light guide 16 results in a greater amount of light being delivered to the sample as well as a more even illumination distribution independent of the distance between the sample aperture and the detector.

Figure 8:
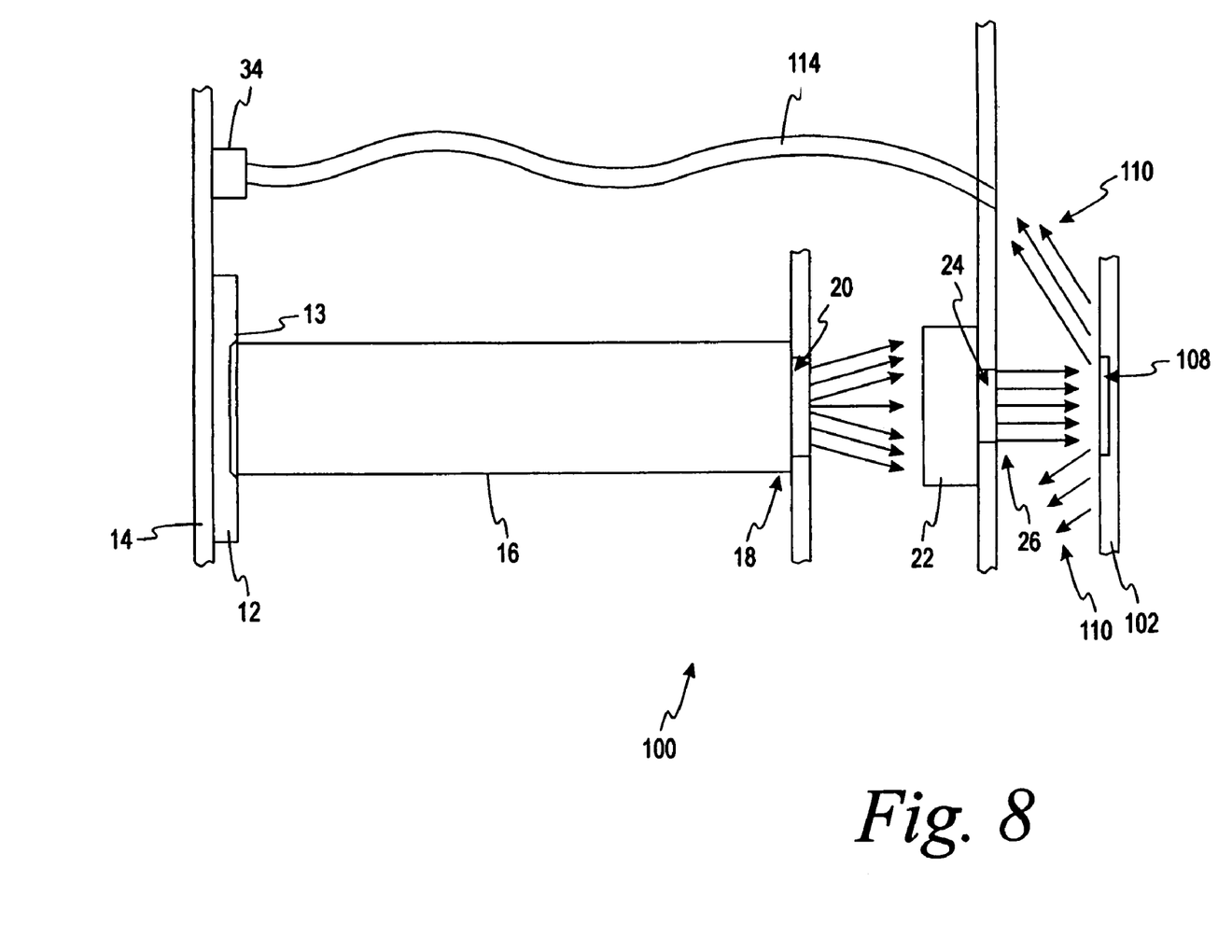
FIG. 8 is a functional block diagram of a multiwavelength reflectance readhead according to an alternative embodiment of the present invention.

Referring to FIG. 8, a multiwavelength diffuse reflectance readhead ("reflectance readhead") 100 is shown according to an alternative embodiment of the present invention. Like the multiwavelength transmission readhead 10 shown in FIGS. 1–3, the reflectance readhead 100 includes the SMD LED 12, disposed on the PCB 14, for inputting light at a plurality of wavelengths to the light guide 16. The light is guided down the light guide 16 though total internal reflection to collimation optics including the collimation aperture 20 and the collimation lens 22 which outputs a substantially collimated beam of light 26 to a sample format 102. The light 26 illuminates a sample disposed in a read area 108 of the sample format 102. The sample format 102, or at least the read area 108 of the format, is constructed of a diffusely reflective membrane such as, for example, paper or a film of polystyrene beads. According to one embodiment of the present invention, the light guide 16 of the reflectance readhead 100 has a square cross section similar to that described in connection with the transmission readhead 10 shown in FIG. 1.

The light 26 scatters off of the sample; this scattered light is referred to with reference number 110. The scattered light 110 includes light reflected off of the surface of the sample, reflected from within the sample, and light reflected off the sample read area 108 of the format 102. Some of the scattered light 110 is collected by a fiber optic cable 114, which pipes the collected scattered light back to a detector 34. According to one embodiment of the present invention, the fiber optic cable 114 has a numerical aperture about 0.51, which translates to a viewing area that is limited to an approximately 30° acceptance cone that overviews the approximately one millimeter sample. The scattered light 110 falling within the acceptance cone of the fiber optic cable 114 is piped back to the detector 34.

Diffuse reflectance accuracy problems are caused by mechanical alignment variation of the optical components. Further, sample beam diameter, divergence, intensity distribution, and location all contribute to errors. These types of errors and problems are factors that directly impact the accuracy of reflectance based systems. Several components of the reflectance readhead 100 contribute to reducing these types of errors. The light guide 16 having a square cross-section reduces beam geometry variations. The SMD LED 12 outputs a non-uniform intensity distribution which is evened out by the light guide 16 resulting in a substantially identical beam diameter, divergence, and alignment at the sample for each wavelength, regardless of the position of the LED die within the SMD LED 12. The light guide 16 allows for a successive side wall reflections within the light guide 16 which results in a substantially uniform irradiance distribution.

Diffuse reflectance applications are also susceptible to precision problems caused by sample height sensitivity. Sample height sensitivity refers to the amount of reflectance variation caused by the sample format 102 read location or height. For example, the sample location varies between samples and meters, and each location causes a reflectance change verses the nominal sample location resulting in an accuracy error. Reduced sample height sensitivity performance is achieved by illuminating the sample in the read area 108 with the collimated light 26. Collimated light produces less change in the illuminated read area 108 as the sample is moved toward and away from the nominal read height. Similarity, sample tilt sensitivity is also reduced by illuminating the sample with the collimated light 26. Sample tilt refers to the orientation of the sample in the read area 108. For example, the sample in the reaction area 108 may not be held perpendicular to the beam 26, and the variation in tilt can cause performance problems. Additionally, as discussed above, the closed coupling of the light guide 16 and the SMD LED 12 allows for the collection of a significant portion (about 92%) of the light output by the SMD LED 12 to be collected by the light guide 16.

While the invention is susceptible to various modifications and alternative forms, specific embodiments thereof have been shown by way of example in the drawings and herein described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

What is claimed is:

1. A readhead for use in the determination of the concentration of an analyte in a sample, the readhead comprising:
   a read area for receiving the sample;
   a plurality of light emitting elements for outputting light at a plurality of wavelengths;
   a light guide having an input end and an output end, the input end being directly coupled to the plurality of light emitting elements for receiving light output by the plurality of light emitting elements, the input end having a center being offset from the center of at least one of the plurality of light emitting elements, the light guide guiding a substantial portion of the light received to the output end;
   a lens for receiving light from the output end of the light guide and for illuminating the sample with a substantially collimated beam of light; and
   a detector for detecting light from the sample in response to illuminating the sample.

2. The readhead of claim 1 wherein the detector detects light transmitted through the sample.

3. The readhead of claim 1 wherein the detector detects light reflected from the sample.

4. The readhead of claim 1 wherein the read area is constructed of a substantially optically transparent material.

5. The readhead of claim 1 wherein the read area includes an optically reflective surface.

6. The readhead of claim 1 wherein the light guide is made of a polymer.

7. The readhead of claim 6 wherein the polymer is acrylic.

8. The readhead of claim 1 wherein the light guide follows a substantially linear path between the input end to the output end.

9. The readhead of claim 1 wherein the light guide follows a path having at least one substantially right angle between the input end and the output end.

10. The readhead of claim 1 wherein the light guide has a length of at least about five centimeters.

11. The readhead of claim 1 wherein the light guide has a substantially square cross-section.

12. The readhead of claim 1 wherein the plurality of light emitting elements is disposed in a surface mount device.

13. The readhead of claim 1 further comprising a printed circuit board, wherein the detector and the light emitting elements are mounted on the printed circuit board.

14. The readhead of claim 1 further comprising a fiber optic cable for delivering the light from the sample to the detector.

15. The readhead of claim 1 wherein the substantially collimated beam of light that illuminates the sample has a substantially uniform cross-section.

16. The readhead of claim 1 further comprising a body having a collimating aperture for reducing the diameter of light output from the output end of the light guide, the body being disposed between the output end of the light guide and the lens.

17. The readhead of claim 1 further comprising a body having a sample aperture for reducing the diameter of the substantially collimated light that illuminates the sample, the body having the sample aperture being disposed between the lens and the read area.

18. The readhead of claim 1 wherein the plurality of light emitting elements for outputting light at a plurality of wavelengths comprises three light emitting elements.

19. The readhead of claim 18 wherein one of the three light emitting elements outputs red light.

20. The readhead of claim 18 wherein one of the three light emitting elements outputs green light.

21. The readhead of claim 18 wherein one of the three light emitting elements outputs blue light.

22. The readhead of claim 18 wherein one of the three light emitting elements outputs light has a wavelength ranging between about 600 nanometers and about 670 nanometers.

23. The readhead of claim 18 wherein one of the three light emitting elements outputs light has a wavelength ranging between about 520 nanometers and about 520 nanometers.

24. The readhead of claim 18 wherein one of the three light emitting elements outputs light has a wavelength ranging between about 360 nanometers and about 450 nanometers.

25. The readhead of claim 18 wherein one of the three light emitting element outputs infrared light.

26. The readhead of claim 18 wherein one of the three light emitting elements output light has a wavelength ranging between about 800 nanometers and about 1000 nanometers.

27. The readhead of claim 1 wherein the sample is a biological sample.

28. A readhead for use in the determination of the concentration of an analyte in a sample, the readhead comprising:
   a read area for receiving the sample;
   a plurality of light emitting elements for outputting light at a plurality of wavelengths;

a light guide having an input end and an output end, the input end being directly coupled to the plurality of light emitting elements for receiving light output by the plurality of light emitting elements, the input end having a center being offset from the center of at least one of the plurality of light emitting elements, the light guide guiding a substantial portion of the light received to the output end;

a lens for receiving light from the output end of the light guide and for illuminating the sample with a substantially collimated beam of light; and a detector for detecting light from the sample in response to illuminating the sample, the sample being a biological sample, wherein the biological sample is blood.

29. A device for measuring the concentration of an analyte in a biological sample, the device comprising:

a test strip for receiving the biological sample, the test strip including a reaction area having a reagent for reacting with the biological sample for producing a colorimetric reaction indicative of the concentration of the analyte in the blood sample;

a test strip receiving area for receiving at least the reaction area of a test strip; and a readhead for use in measuring the degree of color change in the colorimetric reaction, the readhead comprising:

a light source including a plurality of light emitting elements for outputting light at a plurality of wavelengths;

a light guide having an input end and an output end, the input end being directly coupled to the light source for receiving light output by the plurality of light emitting elements, the input end having a center that is offset from the center of at least one of the plurality of light emitting elements, the light guide guiding a substantial portion of the light received to the output end;

a collimating lens for receiving light from the output end of the light guide and for illuminating the reaction area of the test strip with a substantially collimated beam of light; and a detector for detecting light from the reaction area in the test strip that contains the biological sample including the analyte that has reacted with the regent.

30. The device of claim 29 wherein the detector detects light transmitted through the reacted sample.

31. The device of claim 29 wherein the detector detects light reflected from the reacted sample.

32. The device of claim 29 wherein the light guide is made of acrylic.

33. The device of claim 29 wherein the light guide follows a substantially linear path between the first end and the second end of the light guide.

34. The device of claim 29 wherein the light guide follows a path has at least one substantially right angle between the first end and the second end of the light guide.

35. The device of claim 29 wherein the light guide has a substantially square cross-section.

36. The device of claim 29 wherein the light source is a surface mount device.

37. The device of claim 29 wherein each of the plurality of light emitting elements is a light emitting diode.

38. The device of claim 29 further comprising a printed circuit board, wherein the detector and the light source are mounted on the printed circuit board.

39. The device of claim 29 further comprising a fiber optic cable for delivering the light from the reacted sample to the detector.

40. The device of claim 29 wherein the substantially collimated beam of light that illuminates the biological sample has a substantially uniform cross section.

41. The device of claim 29 further comprising a body having a collimating aperture for reducing the diameter of light output from the output end of the light guide, the body being disposed between the output end of the light guide and the collimating lens.

42. The device of claim 29 further comprising a body having a sample aperture for reducing the diameter of the substantially collimated light that illuminates the sample, the body having the sample aperture being disposed between the collimation lens and the read area.

43. The device of claim 29 wherein the plurality of light emitting elements for outputting light at a plurality of wavelengths comprises three light emitting elements.

44. The device of claim 43 wherein one of the three light emitting elements outputs red light.

45. The device of claim 43 wherein one of the three light emitting elements outputs green light.

46. The device of claim 43 wherein one of the three light emitting elements outputs blue light.

47. The device of claim 43 wherein one of the three light emitting elements outputs light has a wavelength ranging between about 600 nanometers and about 670 nanometers.

48. The device of claim 43 wherein one of the three light emitting elements outputs light has a wavelength ranging between about 520 nanometers and about 520 nanometers.

49. The device of claim 43 wherein one of the three light emitting elements outputs light has a wavelength ranging between about 360 nanometers and about 450 nanometers.

50. A method for determining the concentration of an analyte in a biological sample using a multiwavelength readhead to measure a colorimetric reaction between a reagent and the analyte in the biological sample, the method comprising the acts of:

reacting a biological sample including the analyte with the reagent in a read area of the readhead;

illuminating the read area with a plurality of light beams of a plurality of wavelengths;

transmitting the plurality of light beams to the read area with a light guide, the light guide being directly coupled to a plurality of light emitting elements;

substantially collimating the light beams prior to illuminating the sample; and detecting the optical response of the sample including the analyte that has reacted with the reagent to illuminating the read area.

51. The method of claim 50 wherein detecting further comprises detecting light transmitted though the reacted sample in the read area.

52. The method of claim 50 wherein detecting further comprises detecting light reflected from the reacted sample in the read area.

53. The method of claim 50 wherein substantially collimating further comprises reducing the diameter of the plurality of light beams with a collimation aperture disposed in a body.

54. The readhead of claim 50 wherein the read area is constructed of a substantially optically transparent material.

55. The readhead of claim 50 wherein the read area includes an optically reflective surface.

56. The method of claim 50 further comprising reducing the diameter of the substantially collimated light beams with a sample aperture disposed in a body.

57. The method of claim 50 wherein the light guide has a substantially square cross-section.

58. The method of claim 50 wherein the light guide is constructed of a acrylic.

59. The method of claim 49 wherein illuminating further comprises illuminating the read area with three beams of light.

60. The method of claim 59 wherein one of the three beams of light comprises red light.

61. The method of claim 59 wherein one of the three beams of light comprises green light.

62. The method of claim 59 wherein one of the three beams of light comprises blue light.

63. The method of claim 59 wherein one of the three beams of light has a wavelength ranging between about 600 nanometers and about 670 nanometers.

64. The method of claim 59 wherein one of the three beams of light has a wavelength ranging between about 520 nanometers and about 520 nanometers.

65. The method of claim 59 wherein one of the three beams of light has a wavelength ranging between about 360 nanometers and about 450 nanometers.

66. The readhead of claim 18 wherein one of the three light emitting element outputs infrared light.

67. The readhead of claim 18 wherein one of the three light emitting elements output light has a wavelength ranging between about 800 nanometers and about 1000 nanometers.

* * * * *